US 6,659,772 B2

(12) United States Patent
Margeas et al.

(10) Patent No.: US 6,659,772 B2
(45) Date of Patent: Dec. 9, 2003

(54) PROVISIONAL RESTORATIONS FOR HUMAN TEETH AND METHOD

(75) Inventors: Robert C. Margeas, Des Moines, IA (US); Robert L. Nixon, Agoura Hills, CA (US)

(73) Assignee: Cosmedent, Inc., Chicago, IL (US)

( * ) Notice: Subject to any disclaimer, the term of this patent is extended or adjusted under 35 U.S.C. 154(b) by 0 days.

(21) Appl. No.: 09/791,353

(22) Filed: Feb. 23, 2001

(65) Prior Publication Data

US 2002/0119424 A1 Aug. 29, 2002

(51) Int. Cl.[7] .................................................. A61C 5/00
(52) U.S. Cl. ........................................ 433/215; 433/223
(58) Field of Search ................................ 433/215, 226, 433/218, 219, 180, 223

(56) References Cited

U.S. PATENT DOCUMENTS

| 5,549,476 A | * | 8/1996 | Stern | 433/222 |
| 5,676,543 A | * | 10/1997 | Dragan | 433/136 |
| 5,728,633 A | * | 3/1998 | Jacobs | 442/148 |
| 6,022,218 A | * | 2/2000 | Alpert | 433/215 |
| 6,186,790 B1 | * | 2/2001 | Karmaker et al. | 433/215 |
| 6,334,775 B2 | * | 1/2002 | Xu et al. | 433/228.1 |

* cited by examiner

Primary Examiner—Kevin Shaver
Assistant Examiner—Melba Bumgarner
(74) Attorney, Agent, or Firm—Michael Best & Friedrich LLC

(57) ABSTRACT

The present invention relates to a method for preparing provisional veneers for human teeth. An impression matrix of the teeth-receiving provisional veneers is created and the teeth prepared by removal of the enamel to an appropriate depth. The impression matrix is then trimmed to expose the cervical portion of the prepared teeth. The shells of the impression matrix corresponding to each of the prepared teeth are filled with a flowable composite resin and the filled impression matrix is seated over the prepared teeth. The excess flowable composite resin is removed from the cervical portion of the prepared teeth and the remaining flowable composite resin is cured to form the incisal portion of the provisional veneers. The cervical portion of the provisional veneers is then free-form sculpted by applying a sculptable composite resin to the prepared teeth, then curing the sculptable composite resin. The provisional veneers are then fine-finished and polished.

20 Claims, 3 Drawing Sheets

PROVISIONAL RESTORATIONS FOR HUMAN TEETH AND METHOD

FIELD OF THE INVENTION

The present invention relates to restorative dentistry and especially to provisional dental restorations for human teeth.

BACKGROUND OF THE INVENTION

Porcelain and porcelain-metal dental restorations such as veneers, crowns, inlays and onlays are often used to correct or reconstruct the length, size, shape, alignment, occlusion or color of teeth. The use of porcelain restorations provides several advantages, including life-like appearance and superior wear resistance. However, porcelain restorations cannot be prepared by the dentist, but must be fabricated by laboratories, which significantly increases the time and expense involved. Furthermore, porcelain restorations are often difficult to work with, due to the thinness and fragility of the material.

Thus, temporary or provisional restorations made of composite resins are often prepared by the dentist to assess fit and appearance before fabricating definitive porcelain restorations. These provisional restorations also provide the patient with an aesthetic substitute in the interim, while the porcelain restoration is being fabricated by the laboratory.

Methods of preparing provisional restorations using composite resins are well known in the art. For example, in the case of provisional veneers, such methods involve taking a pretreatment impression of the teeth-receiving provisional veneers to create an impression matrix that serves as a template for preparing the provisional veneers. Once the impression matrix has been formed, the teeth-receiving provisional veneers are prepared by reducing the teeth, using the impression matrix as a check to ensure that there is adequate clearance between the prepared tooth and the impression matrix.

The shells of the impression matrix corresponding to the teeth-receiving provisional veneers are filled with a light-curable flowable composite resin and then seated over the prepared teeth. The composite resin is light-cured through the impression matrix, which is then removed to reveal the provisional veneers.

One shortcoming to such prior art methods of preparing provisional veneers is that, as the filled impression matrix is seated over the prepared teeth, excess composite resin is expressed into the gingival margin of the prepared teeth and over adjacent teeth and gum. Upon curing, the excess composite resin forms a flash covering the gingival margin of the prepared teeth, as well as the adjacent teeth and gum.

To avoid initiating marginal gingivitis, this flash must be removed and the cervical finish line of the provisional veneer very accurately adapted to the prepared teeth at the gingival margin. However, removal of this flash requires the use of aggressive finishing burs and is almost impossible to accomplish without damaging the cervical finish line or gingival tissue at the gingival margin. Furthermore, flash below the gum line is inaccessible and cannot be effectively removed. In addition, the removal of flash also involves the risk of nicking or otherwise damaging adjacent teeth.

Thus, there is a reluctance to disturb the provisional veneers at the gingival margin, and provisional veneers are typically left with overhangs at the cervical finish line, which invariably results in marginal gingivitis. This is a highly undesirable condition to have present during the subsequent cementation of the definitive porcelain veneers.

Another problem with such prior art methods is that the resulting provisional restorations cannot accurately reproduce the polychromatic color gradation of natural teeth. Typically, the cervical portion of natural teeth has a darker color shade than the incisal portion. Because the provisional restorations are prepared from a single composite resin, they are uniformly colored and may appear artificial.

Thus, it would be desirable to provide a method for preparing provisional restorations in which the cervical finish line of the provisional restoration may be accurately adapted to the prepared teeth at the gingival margin, without risk of damage to the cervical finish line or gingival tissue at the gingival margin, or to adjacent teeth and gums. In addition, there is a need for a method of preparing provisional restorations that accurately reproduces the natural variation in color between the cervical and incisal portions of teeth.

SUMMARY OF THE INVENTION

These needs and other needs are satisfied by the present invention, which comprises a method for preparing provisional restorations, wherein an impression matrix of the teeth-receiving provisional restorations is prepared using a translucent, clear-colored impression material. The teeth receiving provisional restorations are then prepared by reducing the teeth, and applying a dental adhesive to the surface of the prepared teeth.

The impression matrix is then trimmed such that the cervical portion of the prepared teeth is exposed when the impression matrix is fully seated over the prepared teeth. The shells of the trimmed impression matrix corresponding to each of the prepared teeth are filled with a light-curable flowable composite resin, which will form the incisal portion of the provisional veneers. The filled impression matrix is then seated over the prepared teeth, the excess light-curable flowable composite resin is removed from the exposed cervical portion of the prepared teeth, and the remaining light-curable flowable composite resin cured through the translucent, clear-colored impression matrix.

The impression matrix is removed to reveal the newly formed incisal portion of the provisional veneers. A light-curable sculptable composite resin is applied to the cervical portion of the prepared teeth and free-form sculpted to form the cervical portion of the provisional restorations. The sculptable composite resin is then light cured and the provisional restorations completed by fine-finishing and polishing.

DETAILED DESCRIPTION OF THE INVENTION

In accordance with the present invention, a method is described for preparing provisional restorations for human teeth, such as veneers, crowns, inlays and onlays, in which the incisal and cervical portions of the restorations are separately formed, providing distinct advantages over the prior art. In particular, the present method reduces the likelihood of marginal gingivitis and preserves gingival health by ensuring a very accurate adaptation of the cervical finish line of the provisional restoration to the prepared tooth at the gingival margin, without the need for aggressive finishing procedures that risk damage to the cervical finish line and gingival tissue at the gingival margin, as well as adjacent teeth and gum. Furthermore, the present method prevents the introduction of excess composite resin below the gum line, which may also lead to marginal gingivitis. In addition, the present method permits reproduction of the polychromatic color gradient of natural teeth, resulting in provisional restorations with a more life-like appearance.

The method of preparing the provisional restorations of the present invention comprises the general steps of: creating an impression matrix of the teeth-receiving provisional restorations; preparing the teeth-receiving provisional restorations by reducing the teeth; trimming the impression matrix such that the cervical portion of the prepared teeth is exposed when the impression matrix is fully seated over the prepared teeth; filling the shells of the impression matrix corresponding to each of the prepared teeth with a flowable composite resin; seating the filled impression matrix over the prepared teeth; removing the excess composite resin from the cervical portion of the prepared teeth; curing the flowable composite resin through the impression matrix to form the incisal portion of the provisional restorations; applying a sculptable composite resin to the prepared teeth to free-form sculpt the cervical portion of the provisional restorations, curing the sculpted composite resin; and then fine-finishing and polishing the provisional restorations.

Figure 1:
FIG. 1 is a preoperative view of the upper anterior teeth Nos. 6–11 receiving provisional restorations.

FIG. 1 shows a preoperative view of upper anterior teeth receiving provisional restorations. Using the preparation of provisional veneers as an example, an impression matrix is created by taking an impression of the facial surface, proximal surfaces, and one-half of the lingual surface of the teeth-receiving provisional veneers, and one additional tooth on each side of the midline to provide a stop. If a diastemic space closure or an open contact exists in the teeth-receiving provisional veneers, the impression matrix should cover all of the lingual surface of such teeth.

If the pretreatment condition of the teeth-receiving provisional veneers requires modification in length, alignment, sizing or occlusion, the impression matrix should be taken from a sophisticated, life-like mockup model, such as a Master Diagnostic Model, or MDM (Valley Dental Arts, Stillwater, Minn.). In the alternative, the impression matrix may be taken from a wax mockup or composite resin mockup.

Figure 2:
FIG. 2 depicts the preparation of a tray with impression material for forming an impression matrix of the teeth receiving provisional restorations.

As shown in FIG. 2, the impression matrix is preferably formed using a translucent, clear-colored impression material, such as vinyl polysiloxane (available commercially as Clear Affinity—Clinician's Choice, New Milford, Conn.). Use of a translucent, clear-colored impression material permits the transmission of light through the impression matrix to polymerize the light-curable composite resin used to prepare the provisional veneers. It is also preferred that the impression material have a relatively high viscosity, such that the impression matrix may be formed without the use of a tray.

Figure 3:
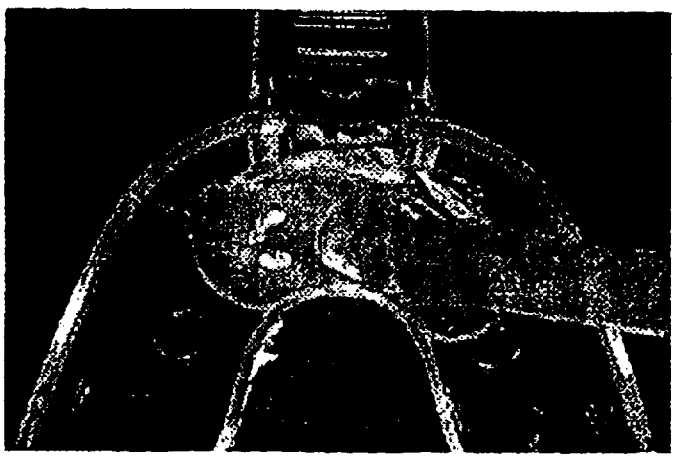
FIG. 3 shows the upper anterior teeth of FIG. 1 after preparation by removal of enamel.

Once the impression matrix has been formed, it is set aside and the teeth prepared for receiving the provisional veneers by removal of the enamel to an appropriate depth. FIG. 3 shows upper anterior teeth Nos. 6–11, which have been prepared by removal of enamel. Typically, the facial surface of the tooth is reduced by approximately 0.5 mm to 1.0 mm. The impression matrix is then placed over the prepared teeth to check the adequacy of the tooth reduction. If the clearance between the prepared teeth and the impression matrix is insufficient, additional reduction of the teeth is undertaken until optimal material requirements, biological contours, occlusal planes and aesthetic outlines are attained.

Once final reductions have been made, the teeth-receiving provisional veneers are further prepared by isolating them from oral contamination by means of rubber dams or cotton rolls, and a high velocity evacuation apparatus. The teeth are then cleaned and disinfected with a 5.25% sodium hypochlorite (Clorox) or chlorhexidine gluconate (commercially available as Consepsis—Ultradent, South Jordan, Utah). The impression matrix is then placed over the teeth to ensure that it is firmly seated on the unprepared teeth on either side of the teeth-receiving provisional veneers and will not move as the provisional veneers are being formed. In addition, a final assessment of the adequacy of tooth reduction is made. If further reductions are made, the teeth are once again cleaned and disinfected before proceeding.

In an alternative embodiment of the present invention, the cleaned and disinfected teeth are further prepared by spot-etching the facial surface of the teeth with 37% phosphoric acid. Spot-etching limits the bonding area between the tooth and the provisional veneer, allowing the provisional veneer to be more easily removed for replacement with a definitive porcelain veneer. The etchant is applied in an approximately 2 mm diameter circle on the mesiodistal center of the facial surface, 2 mm apical to the existing incisal edge, and in enamel if possible. The etchant is left on the teeth for roughly 15 seconds and is then washed away with a thorough 5 second water cleansing. The etched teeth are then carefully dried such that the surface appears moist, rather than bone dry or saturated.

Following preparation of the teeth, a sealant, such as a potassium oxylate chelating agent (available commercially as Super Seal—Phoenix Dental, Fenton, Mich.), may be applied to the surface of the teeth-receiving provisional veneers, to minimize sensitivity due to the presence of exposed dentin with open tubules. Application of a sealant provides interim desensitization of the provisional veneers prior to cementation of the definitive porcelain veneers.

In the final step of preparing the teeth-receiving provisional veneers, a thin coat of an unfilled resin bonding agent, such as Power Bond (Cosmedent, Chicago, Ill.) or All-Bond 2 (Bisco, Itasca, Ill.) is applied over the prepared surfaces of the teeth. The bonding agent should be cured at this time. It may be necessary to protect the wetting agent from premature polymerization by lowering the dental headlight.

Figure 4:
FIG. 4 depicts the trimming of the formed impression matrix of FIG. 3 to reveal the cervical one-third of the teeth receiving provisional restorations.

Once the teeth-receiving provisional veneers have been prepared, the impression matrix is modified by trimming away the cervical one-third of the impression matrix, using a #15 Bard-Parker scalpel (Becton, Dickinson and Company, Franklin Lakes, N.J.) or a pair of small sharp scissors, as shown in FIG. 4. Following trimming, the cervical one-third of the prepared teeth and, in particular, the cervical finish line for the provisional veneers, should be visible and completely accessible when the matrix is fully seated over the prepared teeth. If a tray is used in forming the impression matrix, the tray should be also be relieved using a large acrylic bur, to expose the cervical one-third of the prepared teeth.

Figure 5:
FIG. 5 shows the shells of the teeth receiving provisional restorations in the trimmed impression matrix of FIG. 4, which have been filled with a light-curable, flowable composite resin.

As shown in FIG. 5, the shell of each tooth in the trimmed impression matrix corresponding to a prepared tooth is then three-quarters filled with a light-curable, flowable composite resin, such as R.S.V.P. incisal resin (Cosmedent, Chicago, Ill.). To prevent void spaces in the provisional veneer, the flowable composite resin is applied to the tooth shells using a syringe without a needle or fitted with a large gauge needle—first filling the facial surface and then the incisal edge area of the shell. It is not necessary to completely fill the shell of each prepared tooth in the impression matrix, because there will be excess flowable composite resin once the impression matrix is seated over the prepared teeth.

In alternative embodiments, the light-curable, flowable composite resin may be a microhybrid, microfill, bisacryl, acrylic (such as methyl methacrylate or ethyl methacrylate), or a compomer.

Figure 6:
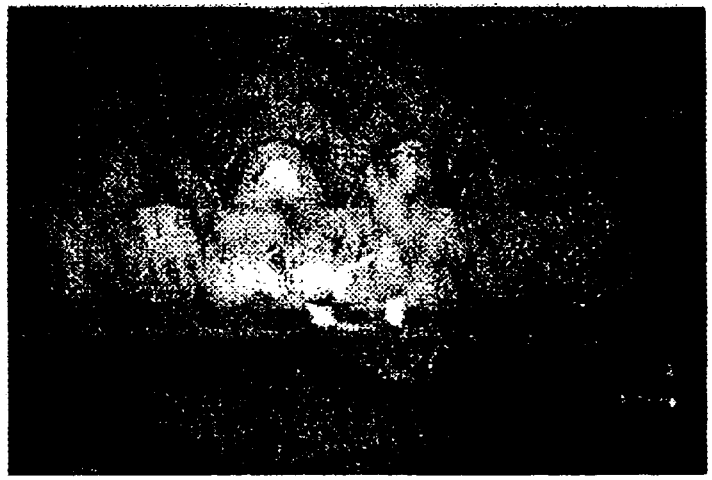
FIG. 6 shows the trimmed and filled impression matrix of FIG. 5 seated over the prepared upper anterior teeth of FIG. 2.

The filled impression matrix is then seated over the prepared teeth, as shown in FIG. 6. Virtually all of the excess flowable composite resin accumulates at the cervical one-third of the facial surface of the prepared teeth. This excess flowable composite resin is carefully removed using non-stick composite placement instruments, such as an IPC-L or IPC-T interproximal carver (Cosmedent, Chicago, Ill.), AccuBrush disposable brushes (Cosmedent, Chicago, Ill.), and/or synthetic fiber brushes (Cosmedent, Chicago, Ill.).

Once the excess flowable composite resin has been removed from the cervical one-third of the prepared teeth and, in particular, the gingival margin, the remaining flowable composite resin inside the shells of the impression matrix is light-cured through the translucent, clear-colored impression material using commercially available polymerizing devices, such as Optilux 501 (Kerr/Demetron, Orange, Calif.). During the light-curing step, it is essential that the impression matrix is held firmly in position between the unprepared teeth on either side of the teeth-receiving provisional veneers.

The flowable composite resin is light-cured as recommended by the manufacturer—in general, approximately 30 seconds, 15 seconds for the facial aspect and 15 seconds for the lingual aspect. The light-curing times may vary according to the power of polymerizing device, curing mode selected and transparency of the impression material, among other factors.

Figure 7:
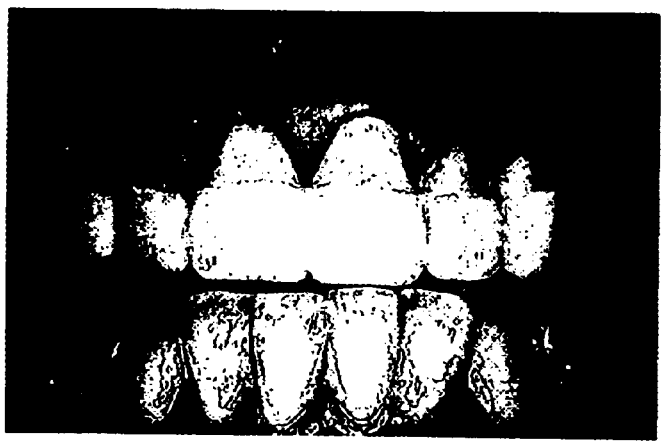
FIG. 7 shows the provisional restorations covering the incisal portion of the prepared upper anterior teeth of FIG. 2, formed after light-curing the flowable composite resin and removal of the impression matrix of FIG. 6.

Following the light-curing step, the modified impression matrix is removed to reveal well contoured provisional veneers, bonded to the prepared tooth surfaces, and covering the incisal portion of the prepared teeth, up to the cervical one-third, as shown in FIG. 7. Because the modification of the impression matrix permits the removal of excess flowable hybrid composite resin from the gingival margin of the prepared teeth, the problem of overbulking or overextending of the provisional veneers along the cervical finish line is eliminated. Any excess provisional material is generally limited to flash at the junction of the cervical one-third and middle one-third of the facial surface. This flash is easily removed with a fine diamond or multi-fluted carbide bur, with little risk of damage to the prepared teeth or gingival tissue at the gingival margin, or to adjacent teeth and gum.

Figure 8:
FIG. 8 depicts the application of a light-curable, sculptable composite resin to the teeth shown in FIG. 7, to form the cervical portion of the provisional restorations.

Following the removal of any excess flash, the cervical one-third of the provisional veneers is formed by applying a light-curable, scultpable composite resin to the cervical one-third of the prepared teeth, as shown in FIG. 8. The scultpable composite resin is free-form sculpted to recreate ideal biological contours and then light-cured as recommended by the manufacturer. If the prepared teeth have a diastemic space closure or an open contact, it is advisable to first block out the lingual half of the "dark triangle" that will occur in the cervical one-third, using a light-curable temporary material, such as E-Z Temp (Cosmedent, Chicago, Ill.), before applying the scultpable composite resin to form the cervical one-third of the provisional veneers.

The ability to free-form sculpt the cervical one-third of the provisional veneers permits a smooth, catchless transition to be created between the cervical finish line of the provisional veneers and the prepared teeth at the gingival margin. Thus, the need for aggressive finishing procedures required by prior art methods is eliminated, thereby avoiding the risk of damage to the prepared teeth and gingival tissue at the gingival margin, and to adjacent teeth and gum. In addition, the junction between the scultpable composite resin and the previously cured incisal portion of the provisional veneers is essentially invisible. As a result, the present method preserves gingival health, is faster and requires less skill than prior art methods.

In a preferred embodiment, the sculptable composite resin is a hybrid composite resin such as R.S.V.P. cervical resin (Cosmedent, Chicago, Ill.). In an alternative embodiment, a microfill, such as Renamel (Cosmedent, Chicago, Ill.), may be used to form the cervical one-third of the provisional veneer. Scultpable hybrid composite resin is, in general, easier to handle than a microfill and does not adapt as firmly to the prepared teeth as a microfill, permitting the provisional veneers to be more easily removed for replacement by definitive porcelain veneers.

In further alternative embodiments, the light-curable, sculptable composite resin may be a microhybrid or a compomer.

Figure 9:
FIG. 9 depicts the polishing of the provisional restorations formed in FIG. 8.

After the cervical one-third of the provisional veneers has been sculpted and light-cured, the provisional veneers are minimally contoured with appropriate fine diamond burs and multi-fluted carbide burs, being careful not to disturb the cervical finish line along the gingival margin. As shown in FIG. 9, the provisional veneers are then fine-finished and polished to a tooth-like luster, using finishing discs, such as FlexiDiscs, FlexiCups, FlexiPoints (Cosmedent, Chicago, Ill.), and polishing discs in conjunction with polishing pastes, such as FlexiBuffs and Renamelize (Cosmedent, Chicago, Ill.), being careful to only polish the cervical finish line at the gingival margin.

The flowable composite resin and sculptable composite resin are commercially available in a range of color shades, to allow for selection of a color shade that accurately reproduces the appearance of the patient's natural teeth. For example, Renamel Flow Hybrid (Cosmedent, Chicago, Ill.) is available in 20 color shades, corresponding to the Vita Shade Guide. To reproduce the polychromatic color gradation of natural teeth, the sculptable composite resin selected to prepare the provisional veneers should be one shade darker than the color shade of the flowable composite resin.

Although the present invention is described as used in preparing provisional veneers, it will be readily understood by those skilled in the art that the present invention may be used to prepare other dental restorations, such as crowns, inlays and onlays.

It will be apparent to those skilled in the art that changes and modifications may be made in the embodiments illustrated herein, without departing from the spirit and the scope of the invention. Thus, the invention is not to be limited to the particular forms herein shown and described except insofar as indicated by the scope of the appended claims.

What is claimed is:

1. A method of preparing a provisional restoration for a human tooth, comprising the steps of:
   preparing an impression matrix forming a shell of the tooth receiving the provisional restoration using an impression material;
   preparing the tooth receiving the provisional restoration by reduction and applying a dental adhesive to the surface of the reduced tooth;
   trimming the impression matrix such that the cervical portion of the prepared tooth is exposed when the impression matrix is fully seated over the prepared tooth;
   forming the incisal portion of the provisional restoration by filling the shell of the impression matrix with a flowable composite resin, seating the impression matrix over the prepared tooth, removing the excess flowable composite resin from the exposed cervical portion of the prepared tooth, and curing the remaining flowable composite resin; and
   forming the cervical portion of the provisional restoration by removing the impression matrix from the newly formed incisal portion of the provisional restoration, applying a sculptable composite resin to the cervical portion of the prepared tooth, and free-form sculpting and curing the sculptable composite resin to form the cervical portion of the provisional restoration.

2. The method of claim 1, further comprising the step of preparing the tooth receiving the provisional restoration by spot-etching the facial surface of the reduced tooth.

3. The method of claim 1, further comprising the step of preparing the tooth receiving the provisional restoration by applying a sealing agent to the entire surface of the tooth receiving the provisional restoration, prior to applying a dental adhesive.

4. The method of claim 1, further comprising the step of finishing and polishing the provisional restoration.

5. The method of claim 1, wherein the provisional restoration is a veneer.

6. The method of claim 1, wherein the provisional restoration is a crown.

7. The method of claim 1, wherein the provisional restoration is an inlay.

8. The method of claim 1, wherein the provisional restoration is an onlay.

9. The method of claim 1, wherein said impression matrix is translucent and clear-colored, and said flowable composite resin is light-curable, whereby said incisal portion of the provisional restoration is formed by light-curing said light-curable flowable composite resin through said translucent, clear-colored impression matrix.

10. The method of claim 1, wherein said impression material is vinyl polysiloxane based.

11. The method of claim 1, wherein said dental adhesive is an unfilled resin bonding agent.

12. The method of claim 1, wherein said flowable composite resin is a hybrid composite resin.

13. The method of claim 1, wherein said flowable composite resin is selected from the group consisting of hybrid composite resins, microhybrid composite resins, microfills, bisacryls, acrylics, and compomers.

14. The method of claim 13, wherein said flowable composite resin is light-curable.

15. The method of claim 1, wherein said sculptable composite resin is a hybrid composite resin.

16. The method of claim 1, wherein said sculptable composite resin is selected from the group consisting of hybrid composite resins, microfills, microhybrid composite resins, and compomers.

17. The method of claim 16, wherein said sculptable composite resin is light-curable.

18. The method of claim 1, wherein said flowable composite resin is selected from a plurality of flowable composite resins in a range of color shades.

19. The method of claim 18, wherein said sculptable composite resin is selected from a plurality of sculptable composite resins in a range of color shades.

20. The method of claim 19, wherein said selected sculptable composite resin is a color shade that is darker than the color shade of said selected flowable composite resin.

* * * * *